United States Patent [19]

Buchholz

[11] 4,410,731

[45] Oct. 18, 1983

[54] PROCESS FOR THE MANUFACTURE OF METHYL MERCAPTAN FROM CARBON OXIDES

[75] Inventor: Bernard Buchholz, Blue Bell, Pa.

[73] Assignee: Pennwalt Corporation, Philadelphia, Pa.

[21] Appl. No.: 334,034

[22] Filed: Dec. 23, 1981

Related U.S. Application Data

[63] Continuation-in-part of Ser. No. 212,942, Dec. 4, 1980, abandoned, which is a continuation of Ser. No. 11,977, Feb. 14, 1979, abandoned, which is a continuation-in-part of Ser. No. 883,438, Mar. 6, 1978, abandoned.

[51] Int. Cl.[3] .......... C07C 148/00

[52] U.S. Cl. .......... 568/70

[58] Field of Search .......... 568/69, 70

[56] References Cited

U.S. PATENT DOCUMENTS

| | | | |
|---|---|---|---|
| 2,820,062 | 1/1958 | Folkins et al. | 568/70 |
| 3,006,966 | 10/1961 | Doumani | 568/70 |
| 3,035,097 | 5/1962 | Deger et al. | 568/70 |
| 3,070,632 | 12/1962 | Olin et al. | 568/70 |
| 3,488,739 | 1/1970 | van Venrooy | 568/70 |
| 3,792,094 | 2/1974 | Hanson | 568/70 |
| 3,880,933 | 4/1975 | Kubicek | 568/70 |
| 3,994,980 | 11/1976 | Kubicek | 568/70 |
| 4,005,149 | 1/1977 | Kubicek | 568/70 |

OTHER PUBLICATIONS

Chem. Abstracts, General Subject Index, 1972–1976, p. 2321GS.

*Primary Examiner*—Donald G. Daus
*Assistant Examiner*—M. C. Eakin

[57] ABSTRACT

A process is provided for the manufacture of methyl mercaptan by reacting a carbon oxide, hydrogen sulfide and hydrogen in the presence of a catalyst at elevated temperature and pressure; the catalyst is a single-phase, solid material comprising a porous alumina-containing support upon which is deposited a mixture of one or more selected metallic sulfides and an alkali metal sulfide.

8 Claims, No Drawings

PROCESS FOR THE MANUFACTURE OF METHYL MERCAPTAN FROM CARBON OXIDES

BACKGROUND

Cross-References

This is a continuation-in-part of copending application Ser. No. 212,942, filed Dec. 4, 1980, now abandoned, which is a continuation of application Ser. No. 011,977, filed Feb. 14, 1979, now abandoned, which is a continuation-in-part of application Ser. No. 883,438, filed Mar. 6, 1978, now abandoned.

PRIOR ART DISCUSSION

Methyl mercaptan is a well known article of commerce used as an intermediate for the manufacture of a variety of agricultural chemicals, including methionine, a widely used feed supplement for poultry. The current preferred commercial method for manufacturing methyl mercaptan is by reaction of methanol and hydrogen sulfide. A variety of catalysts can be used such as thoria, zirconia, activated aluminas, silica-aluminas, and alumina promoted tungstates or molydates (U.S. Pat. No. 2,820,062) or heteropoly acids or their salts (U.S. Pat. Nos. 3,035,097). These processes, as practiced commercially, are efficient and provide methyl mercaptan in high yield and purity.

Nevertheless, further economy can be achieved by the use of the more basic raw materails carbon monoxide or carbon dioxide in place of methanol according to the following equations:

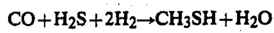

$$CO+H_2S+2H_2 \rightarrow CH_3SH+H_2O$$

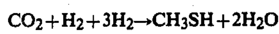

$$CO_2+H_2+3H_2 \rightarrow CH_3SH+2H_2O$$

U.S. Pat. No. 3,070,632 dated Dec. 25, 1962, discloses and claims a process using a two-phase catalyst system wherein the reaction proceeds in accordance with the above equations, however this method has a number of shortcomings from a commercial viewpoint. The yields are rather low. Further, the two-phase catalyst system employes a complex system wherein a relatively large amount of powdered sulfactive hydrogenation catalyst (compared to the reactants employed) is suspended in a large volume of a liquid organic amine. Still further, the preferred reaction conditions require operating at high pressures (1200 to 2000 psig) over long reaction periods (3 to 6 hours). In addition, the amine co-catalyst produces hydrosulfide salts at the recited reaction conditions and these salts are unstable at standard atmospheric conditions, decomposing into highly toxic hydrogen sulfide gas.

The above mentioned patent also includes a disclosure (Example IX) of vapor-phase reaction of a mixture of carbon oxide, hydrogen sulfide and hydrogen wherein the reactants are passed at elevated temperature through a single-phase, solid catalyst system (NiS on $Al_2O_3$). The catalyst is sulfided before use. No conversion or yield results are given.

STATEMENT OF INVENTION

This invention is a continuous process for the manufacture of methyl mercaptan by contacting a carbon oxide, sulfur or hydrogen sulfide, and hydrogen at elevated temperature and pressure at least sufficient to maintain sulfur in the molten state and at a carbon oxide space velocity of between about 5 and about 200 with a preformed, single-phase, solid catalyst system comprising from about 10 to about 90%, based on the weight of the catalyst system, of a porous alumina-containing support upon which is deposited from about 10 to about 90%, based on the weight of said system, of a mixture of (a) from about 65 to about 95 percent, based on the weight of the mixture, of at least one sulfide selected from the group consisting of sulfides of iron, nickel, zinc, chromium, cobalt and molybdenum, and (b) from about 5 to 35 percent, based on the weight of the mixture, of an alkali metal sulfide.

This invention also comprises the single-phase, solid catalyst system as described above and the method of preparing it.

DEFINITIONS

Certain terms and phrases used herein have the following meaning with regard to this disclosure.

The term "single-phase, solid catalyst" means a catalytically active mass of intimately mixed components which are solid materials.

The term "hydrogenation catalyst" as used herein means the sulfides of iron, nickel, zinc, chromium, cobalt, molybdenum and mixtures of these sulfides. This term also includes the oxides, hydroxides and salts of the above mentioned metals prior to and after sulfiding whereby they are least partially converted to the sulfide. The hydrogenation catalyst can consist of more than one of the metals named above, e.g., zinc and chromium, which on sulfiding may consist of either a simple mixture of sulfides, a complex sulfide or both.

The term "promoter" as used herein means alkali metal sulfides and hydrosulfides or alkali metal oxides, hydroxides or salts prior to or after sulfiding.

The term "catalyst system" as used herein means the combined hydrogenation catalyst, promoter and support.

The term "sulfide" as used herein is defined as a material including simple sulfides and hydrosulfides, and complex sulfides which may contain more than one of the metals described herein.

The term "sulfiding" or "sulfided" as used herein relates to the treatment of the supported mixture of hydrogenation catalyst and promoter, at least one of which is not in the sulfide state, with hydrogen sulfide or vaporous elemental sulfur under elevated temperature for a time such that the mixed materials are at least partially converted to the sulfide. Conversion of either the hydrogenation catalyst or the promoter from the oxide, hydroxide or salt to the sulfide state will change with weight of the compound somewhat but generally will permit, prior to the sulfiding, the use of the sulfide precursor within the same weight range as described herein for the sulfide in order to provide a catalyst system as defined for this invention.

The term "space velocity" as used herein, refers to the volume (e.g., liters) of carbon oxide passing through a unit volume (e.g., liter) of the catalyst system during one hour measured at standard temperature and pressure.

EXAMPLES

The improved process for the production of methyl mercaptan is illustrated by the following examples:

EXAMPLE 1

A number of catalysts of this invention are evaluated using a fixed catalyst bed, vertical, tubular, continuous reactor. The catalysts are prepared by mixing 5 parts by weight of an alkali metal hydroxide or salt with 95 parts by weight of commercial catalyst consisting of nickel oxide on an alumina support and then sulfiding by passing hydrogen sulfide over the mixture for six hours at atmospheric pressure and a temperature of 370° C. The activated alumina supported nickel oxide which is used (Harshaw Ni-0301T) contains 11% by weight (based on NiO-alumina) of nickel present as oxide, has a surface area of 64 sq. meters per gram, a pore volume of 0.32 cc per gram, an average bulk density of 70 lbs. per cubic foot and is in the form of ⅛-inch thick tablets.

The reactants, carbon monoxide, hydrogen sulfide and hydrogen, are mixed at ambient temperature just prior to being passed downward through the vertically mounted, catalyst-containing reactor. The molar ratio of the reactants in the mixture, $CO/H_2S/H_2$, for all runs except Run No. 1, is 1/8/4. The molar ratio in Run No. 1 is 1/4/4. The reactants in each run are passed through the reactor at a controlled space velocity measured at 5 liters of carbon monixide per liter of catalyst per hour. The pressure during each run is maintained at 175 psig by an automatic back-pressure regulator, and the crude product stream is passed as a vapor through heated lines at atmospheric pressure into the gas-sampling device of a gas chromatograph for analysis. The single-pass conversions and yields of carbon monoxide to methyl mercaptan (MM) are calculated from the gas chromatographic analyses.

Table 1 below shows the reaction conditions, conversions and yields to MM. All runs are of at least 15 hours duration. The yield figures take into account only the unreacted CO (carbon monoxide) remaining in the crude product after a single pass through the reactor and do not include by-products such as carbon dioxide, carbonyl sulfide, and carbon disulfide which would, in a commercial operation, be recycled to produced additional MM with high ultimate yields.

TABLE 1

| Run No. | Promoter 5 p.p.h.* | Catalyst Bed temp., °C. | Av. % Conversion CO → MM | Av. % Yield CO → MM |
|---|---|---|---|---|
| 1 | None | 278 | 20 | 24 |
| 2 | $Na_2CO_3$ | 275 | 25 | 33 |
| 3 | NaOH | 275 | 30 → 16** | 36 → 32** |
| 4 | KOH | 275 | 40 | 41 |
| 5 | $K_2CO_3$ | 280 | 39 | 41 |
| 6 | $K_2WO_4$ | 280 | 37 | 38 |
| 7 | KPT*** | 284 | 35 | 38 |
| 8 | $K_2C_2O_4$ | 288 | 39 | 40 |
| 9 | $KC_2H_3O_2$ | 285 | 38 | 41 |
| 10 | $RbC_2H_3O_2$ | 285 | 36 | 39 |
| 11 | $CsC_2H_3O_2$ | 282 | 43 | 44 |
| 12 | $Cs_2CO_3$ | 287 | 44 | 45 |
| 13 | CsOH | 290 | 46 | 47 |
| 14 | $Ca(C_2H_3O_2)_2$ | 293 | 11 | 18 |

*Parts promoter per hundred parts by weight of the total catalyst system.
**Conversion and yield decreased with time.
***KPT: potassium phosphotungstate.

The data of the above table serve to permit comparison of the effectiveness of the various promoters used under similar process conditions. In Run No. 1, no promoter is used with the sulfide nickel oxide on alumina support and in Run No. 14, an alkaline earth metal promoter is used in place of the alkali metal promoter. In both runs the results are inferior to the runs wherein the alkali metal sulfide promoter is employed.

EXAMPLE 2

The same equipment, operating procedure, reactants and reaction conditions, except for the catalyst system and catalyst bed temperature, are employed in this example to investigate the promoter effect of various levels of sulfided cesium hydroxide in this invention. The catalyst is prepared by mixing amounts varying from 1 to 10 parts of cesium hydroxide with 99 to 90 parts of the alumina support bearing nickel oxide and sulfiding the mixture as described in Example 1.

The results of this investigation are given in Table 2. The conversions and yields for this and succeeding examples are determined in the same manner as in Example 1.

TABLE 2

| Run No. | Promoter (p.p.h.*) | Catalyst bed Temp. °C. | Av. % Conversion CO → MM | Av. % Yield CO → MN |
|---|---|---|---|---|
| 1 | 1 | 288 | 31.1 | 34.2 |
| 2 | 2.5 | 286 | 37.8 | 40.4 |
| 3 | 5 | 290 | 46.9 | 47.6 |
| 4 | 10 | 290 | 39.8 | 42.5 |
| 5 | " | 302 | 43.7 | 45.2 |
| 6 | " | 313 | 44.5 | 45.7 |
| 7 | " | 318 | 45.4 | 47.3 |
| 8 | " | 331 | 44.6 | 45.4 |

*p.p.h. = parts CsOH per hundred parts by weight of the total catalyst system.

The data of Table 2 show that the optimum amount of this promoter on the nickel-bearing alumina support is about 5 p.p.h., based on the weight of the catalyst system, at a catalyst bed temperature of 290° C.

EXAMPLE 3

A fixed bed, tubular, horizontal reactor equipped with a reactant preheater, and the reactions of Example 1, are used for additional runs varying process conditions as reported in Table 4. The molar ratios of the reactant mixture, $CO/H_2S/H_2$, for all runs except Runs 10 and 11, is 1/8/8. The molar ratio for Runs 10 and 11 is 1/8/4. The space velocity as defined herein before is 5 for all runs except Run No. 9 in which the space velocity is 10. These runs exemplify the effect of preheating the reactants and the use of high reaction pressures (400–1000 psig.) The two catalyst systems employed for this example are prepared with the materials and procedure described in Example 1, the promoter being 5 p.p.h. of KOH or CsOH as indicated. The results obtained for these runs are reported in the following table.

TABLE 3

| Run No. | Pressure, psig. | Preheater temp., °C. | Cat. bed Temp., °C. | Avg. % Conv. CO → MM | Avg. % Yield CO → MM |
|---|---|---|---|---|---|
| | Presulfided KOH Catalyst System | | | | |
| 1 | 400 | 100 | 275 | 43.4 | 50.4 |
| 2 | 1000 | 100 | 282 | 64.6 | 66.8 |
| 3 | 600 | 100 | 290 | 52.0 | 54.9 |
| 4 | 700 | 100 | 291 | 62.0 | 63.8 |
| 5 | 400 | 100 | 292 | 56.7 | 57.7 |
| 6 | 1000 | 100 | 292 | 63.7 | 66.2 |
| 7 | 700 | 100 | 285 | 76.1 | 77.6 |
| 8 | 700 | 300 | 292 | 82.6 | 83.3 |
| 9 | 700 | 300 | 290 | 59.5 | 62.0 |
| 10 | 700 | 300 | 290 | 86.3 | 86.5 |

TABLE 3-continued

| Run No. | Pressure, psig. | Preheater temp., °C. | Cat. bed Temp., °C. | Avg. % Conv. CO → MM | Avg. % Yield CO → MM |
|---|---|---|---|---|---|
| | Presulfided CsOH Catalyst System | | | | |
| 11 | 700 | 300 | 290 | 90.2 | 90.2 |

A comparison of the results between Runs 1 and 2 of the above table demonstrates that an increase in reactor pressure, other process condition remaining substantially the same, produdes an increase in conversion and yield percentage. Runs 3 and 4, and Runs 5 and 6, show that an increase in reactor pressure increases conversion and yield percentages when other process conditions remain the same. At the pressures shown in the table (400–1000 psig.) the by-product $CO_2$, as well as CO, is converted to MM thereby achieving high conversions and yields. The by-product $CO_2$ apparently reacts slowly with $H_2S$ and $H_2$ at low pressures, but more rapidly at the pressure shown in the table.

A comparison of the results in Runs 7 and 8 indicate that an increase in the preheater temperature from 100° to 300° C. whereby the temperature of the reactants is increased before they are fed to the reactor, provides an increase in conversion and yield under otherwise similar reaction conditions. The results for Run 9 compared to those of Run 8 show that increased CO space velocity (from 5 to 10) will produce a decrease in conversion and yield. Finally, Run 11, which was conducted under the same process conditions as Run 10, except for the catalyst system emloyed, produces an improvement in conversion and yield with the preferred sulfided cesium hydroxide promoter.

EXAMPLE 4

Another series of runs is carried out wherein the carbon monoxide space velocity is increased from run to run (except for runs 3, 4 and 5). The runs are conducted with the equipment and reactants of Example 3 with the procedure and conditions modified as reported in the table below. The catalyst system used is the presulfided CsOH—NiO-alumina material of Example 3 and the reaction pressure is 700 psig in all cases. The results are set forth in the following table.

TABLE 4

| Run No. | CO Space velocity* | $CO/H_2S/H_2$ molar ratio | Preheater temp., °C. | Catalyst bed temp., °C. | Avg. % Conversion CO → MM |
|---|---|---|---|---|---|
| 1 | 5 | 1/8/4 | 300° C. | 275 | 89 |
| 2 | 60 | 1/8/4 | 175° C. | 275 | 54 |
| 3 | 60 | 1/6/2 | 204° C. | 275 | 61 |
| 4 | 60 | 1/4/2 | 200° C. | 275 | 57 |
| 5 | 60 | 1/3/2 | 210° C. | 275 | 54 |
| 6 | 120 | 1/6/2 | 180° C. | 299 | 53 |
| 7 | 180 | 1/8/3 | 200° C. | 316 | 49 |

*Liters of carbon monoxide per liter of catalyst per hour.

The data in Table 4 show that fairly high conversions of CO to MM are obtained at commercially practical space velocities in the range of 60 to 180 but as the CO space velocity is increased, the conversion to MM decreases. To maintain the conversions achieved at a space velocity of 60 (Runs 2–5), when increasing the space velocity to 120, it is beneficial to use a slightly higher catalyst bed temperature than those of Runs 2–5 as demonstrated in Run 6. In addition it is found that the amount of by-product $CO_2$ increases with increases in space velocity but the $CO_2$ can be recycled to produce additional MM.

EXAMPLE 5

Carbon dioxide, hydrogen sulfide and hydrogen streams are separately preheated, mixed together at a molar ratio of 1/8/4 respectively and passed continuously into the horizontal reactor and through the presulfided CsOH-NiO-alumina catalyst system of Example 3. The pressure in the reactor is maintained at 700 psig. Other reaction conditions and results are set forth in the following table.

TABLE 5

| $CO_2$ Space velocity (liters/liter) | Preheater temp., °C. | Catalyst bed temp., °C. | Avg. % Conversion $CO_2$ → MM | Avg. % yield $CO_2$ → MM |
|---|---|---|---|---|
| 5 | 185 | 271 | 49 | 87 |
| 5 | 170 | 290 | 46 | 82 |
| 5 | 160 | 290 | 52 | 92 |
| 60 | 170 | 293 | 24 | 58(*) |

(*) Major by-products are CO and COS, which at lower space velocity 5, are apparently converted further to MM.

The results summarized in the above table illustrate that $CO_2$ is also readily converted to MM in the process.

EXAMPLE 6

This example illustrates the use of a preferred catalyst system using the equipment of Example 3. Activated alumina bearing zinc and chromium (Harshaw-Zn-0601T) is used in the preparation of the catalyst system of this example. As analyzed by the supplier, the Harshaw material consists of 38 weight % zinc oxide and 25 weight percent chromium oxide mounted on 37 weight % active alumina; it has an average bulk density of 97 lbs./cu. ft., a surface area of 56 $m^2$/g. and pore volume of 0.18 cc./g. The catalyst system is prepared by impregnating 95 parts by weight of this alumina bearing zinc and chromium material, after calcining in air, with 5 parts by weight of CsOH and sulfiding the impregnated material as described in Example 1.

The reactants CO, $H_2S$ and $H_2$, are preheated to 170° C., combined at a molar ratio respectively of 1/6/4 and fed to the reactor. The feed is passed continuously through the catalyst bed at a carbon monoxide gaseous space velocity of 120 and under a pressure of 700 psig. The catalyst bed temperature is maintained at about 350° C.

Calculations from the gas chromatographic analysis of the crude product stream exiting the reactor after one pass through the catalyst bed show 53% conversion of the CO to MM with no by-product methane formation. Under comparable reaction conditions using the nickel-containing catalyst (See Run 6 of Table 4), comparable conversion to MM is achieved but appreciable conversion (3–5%) of the undesirable by-product methane is also obtained.

EXAMPLE 7

Elemental sulfur is preheated to 285° C. and the liquid sulfur mixed with similarly preheated carbon monoxide and hydrogen. The sulfur immediately reacts with the hydrogen to produce hydrogen sulfide in the reaction chamber and the resulting gaseous feed of carbon oxide, hydrogen sulfide and hydrogen in a molar ration of 1/6/4 passes continuously through the bed of the catalyst system described in Example 6 at a carbon monoxide space velocity of 80. The pressure in the reactor is maintained at 250 psig. and the catalyst bed temperature is about 396° C.

Gas chromatographic analysis of the product stream exiting from the reactor shows a high hydrogen sulfide content, and a 27.6% conversion of the CO to MM. All the sulfur is consumed in one pass through the reactor. Recycling of the hydrogen sulfide formed in the first pass through the reactor, in mixture with CO and $H_2$, will produce additional MM. When the pressure in the reaction of the example is increased to 700 psig. and the space velocity increased to 100, a single pass conversion of 40% of CO to MM is obtained.

EXAMPLE 8

In place of carbon monoxide, carbon dioxide is mixed with hydrogen sulfide and hydrogen at a molar ratio of 1/8/4. The mixture is preheated to a temperature of 300° C. and passed continuously into a reactor containing the catalyst system of Example 6. The carbon dioxide space velocity (as defined for carbon monoxide) is 60. The catalyst bed temperature is about 386° C. and the pressure in the reactor is 700 psig.

Gas chromatographic analysis of the crude product stream exiting from the reactor shows a 42% conversion of $CO_2$ to MM in the single pass, with a yield of 75% (based only on unreacted $CO_2$). Under comparable conditions with the nickel-containing catalyst system (see last Run of Table 5) only 24% conversion of $CO_2$ to MM is achieved in a single pass. Thus, the zinc-chromium containing catalyst system described in Example 6 is almost twice as active as the nickel-containing catalyst system for converting $CO_2$ to MM.

DISCUSSION—GENERIC

The process of this invention is a continuous reaction wherein a mixture of carbon oxide, hydrogen sulfide or elemental sulfur, and hydrogen is subjected to elevated temperature and pressure in the presence of a specified sulfided or sulfide catalyst system to provide methyl mercaptan in improved conversions and yields. A wide range of reaction conditions may be used to obtain conversions to methyl mercaptan in this process. The by-products or unconverted reactants can be separated by distillation from the methyl mercaptan product and recycled to obtain maximum economy in a commercial operation. Generally, higher conversions and yields are obtained with the preferred conditions as set forth below.

The Reactants

Carbon monoxide, elemental sulfur or hydrogen sulfide and hydrogen are the preferred starting materials for the process of this invention. Carbon dioxide may be used to replace part or all of the carbon monoxide but carbon monoxide is more reactive and provides higher conversions than carbon dioxide at high space velocities.

Carbon monoxide and hydrogen reactants may be inexpensively prepared using the well known "synthesis gas" process which proceeds according to the formula:

$$CH_4+H_2O \rightarrow CO+3H_2$$

A supplied hydrogen sulfide may be used in the process or hydrogen sulfide may be formed on site by reacting elemental sulfur in the molten or vapor state with hydrogen to form the hydrogen sulfide either before or after mixing the reactants for feeding to the reactor. Alternatively, elemental sulfur may be fed directly to the reactor with the carbon oxide and hydrogen. Under the temperature and pressure conditions of this process, the sulfur will be in the molten state and will immediately react with hydrogen to form hydrogen sulfide in situ. The chemical equation for the process of this invention when employing elemental sulfur in the feed is one of the following depending on whether CO or $CO_2$ is the carbon oxide of the feed.

$$CO+S+3H_2 \rightarrow CH_3SH+H_2O$$

$$CO_2+S+4H_2 \rightarrow CH_3SH+2H_2O$$

When the preferred starting materials are used, i.e., carbon monoxide, hydrogen sulfide or elemental sulfur, and hydrogen, gas chromatographic analyses of the crude product streams show carbon dioxide to be the major by-product, with small amounts of carbonyl sulfide, dimethyl sulfide and traces of methane also detected. Methane formation is minimized by maintaining the reaction temperature below about 300° C. The remaining by-products are easily separated by distillation. The reaction sequence by which carbon monoxide is converted to methyl mercaptan is:

$$CO+H_2S \rightarrow COS+H_2 \quad (a)$$

$$COS+3H_2 \rightarrow CH_3SH+H_2O \quad (b)$$

Reactions (a) and (b) proceed readily using the preferred catalyst system under the conditions of this process; reaction between CO and $H_2$ to produce methanol does not occur.

Process Conditions

The feed rate of the reactants through the catalyst bed of the reactor is reported herein as space velocity of carbon oxide. The optimum space velocity employed will vary depending upon other conditions of the process such as temperature, pressure and molar ratio of reactants. In general, high conversions are realized with low space velocities. The preferred space velocity range is about 5 to 200. In commercial practice, where high production rates are desired, this process can be operated at high space velocities in the range of 60–200 with relatively high conversions to methyl mercaptan per pass.

The molar ratio of reactants in the feed mixture, i.e., carbon oxide, hydrogen sulfide or elemental sulfur, and hydrogen, is not a critical feature of the process. The ratio of reactants consumed is that theoretically required to form methyl mercaptan by the direct conversion of these reactants. Preferably, the carbon oxide will be fed to the reactor with a molar excess of both hydrogen sulfide and hydrogen. Most preferably, molar ratios of $CO_{1\text{-}2}/H_2S/H_2$ between 1/3/2 and 1/8/8 are used. When utilizing elemental sulfur to replace $H_2S$ in the feed, the molar ratio of the reactants $CO_{1\text{-}2}/S/H_2$ will preferably range from about 1/3/3 to about 1/8/10.

The reactants are preferably mixed in the desired molar ratio before being passed to the reactor but they may also be introduced separately to the reactor at a rate and amount to produce the desired molar ratio and space velocity.

To increase the conversions and yields in the process, the reactants are advantageously preheated either individually or as a mixture prior to entering the reactor. The preferred preheating range is from about 180°to about 300° C.

The elevated temperature and pressure of the process are at least sufficient to maintain sulfur in the molten state. The pressure in the reactor is generally above 150 psig. and preferably within the range of about 400 to about 1000 psig., the pressures of this range increasing the conversion to methyl mercaptan. Temperature in the reactor is generally controlled by the temperature of the catalyst bed which preferably ranges between about 250° C. and 400° C.

The Catalyst System

The catalyst system for the process of this invention is a preformed material, i.e., it is mixed and, if necessary, sulfided prior to the introduction of the process reactants to the reactor. The catalyst system required for the process consists of a hydrogenation catalyst in the sulfide form, a promoter in the sulfide form, and a porous alumina-containing support. The hydrogenation catalyst and promoter, as broadly used in this disclosure, have been defined hereinbefore. The preferred hydrogenation catalysts are those containing sulfide of nickel or zinc and chromium, most preferably the catalyst contains a mixture of from about 50 to about 65 weight % zinc sulfide and from about 35 to about 50 weight % chromium sulfide.

Potassium, rubidium and cesium are the preferred alkali metals, in the sulfide form, for the promoter and cesium is the most preferable.

The hydrogenation catalyst and promoter are carried on a suitable porous alumina-containing support which may be, for example, alumina, silica-alumina, calcium aluminate, kieselguhr, various clays or refractory materials and the like. Alumina, or activated alumina, is the preferred support for the catalyst system. A kieselguhr-supported catalyst system has been employed in this process under the conditions of Example 1 where the kieselguhr carried 67.7% nickel oxide and 5% potassium hydroxide, based on the weight of the catalyst system, and this catalyst system as sulfided before use. When using this kieselguhr-supported catalyst, the reactor pressure was relatively low (175 psig) and less than the desired improvement in conversion and yield was obtained. However, the supports intended to be included herein are those porous materials comprising alumina which are operative as part of a catalyst system which will provide improved results over prior art alumina-supported catalysts in the process of this invention.

The support which carries the catalyst and promoter is preferably from about 10 to about 90 percent by weight of the catalyst system and the hydrogenation catalyst-promoter mixture is present in an amount ranging from 10 to 90% of the catalyst system. The proportion of hydrogenation catalyst used in admixture with the alkali metal promoter preferably ranges from about 65 to about 95 percent, based on the weight of the admixture, while the proportion of the alkali metal promoter ranges from about 5 to about 35 percent.

Usually, an alumina-containing support bearing the hydrogenation catalyst is obtained from a commerical source and impregnated with a solution of the promoter. For example, a preferred catalyst system is prepared with 900–990 grams of a pelletized, supported hydrogenation catalyst consisting of 5–20 weight percent of nickel oxide and 80–95 weight percent activated alumina. This is dried at 150° C. and impregnated with a solution containing 10–100 grams of cesium hydroxide in water. The solution is added slowly with thorough mixing and the wet catalyst is dried overnight in an oven at 150° C.

A procedure for preparing another preferred catalyst system used herein requires that the hydrogenation catalyst bearing zinc and chromium, as described in Example 6 supra, be calcined in air for about 12–20 hours at a temperature in the range of 425°–550° C. After calcining, this material is uniformly treated with an aqueous solution of cesium hydroxide having a weight concentration of about 30–32%. The amount of solution used is just sufficient to saturate the calcined hydrogenation catalyst without causing separation of a water layer on standing. The saturated material, after thorough mixing, is allowed to dry in air, preferably under heat of about 150° C., for about 16 hours. This material should be stored in an air-tight container to prevent pick-up of moisture prior to use. Before use the dried catalyst is sulfided if not in the sulfide form, as described below.

While the hydrogenation catalyst is frequently obtained from the supplier on a support, either the hydrogenation catalyst or the promoter may be first deposited on a support and the other component of the catalyst system subsequently mixed with the supported component or, alternatively, both materials are deposited simultaneously.

Sulfiding the catalyst system is required where one or both of the hydrogenation catalyst and promoter are not in the sulfide form i.e., they are in the oxide, hydroxide or salt form. In carrying out a conventional sulfiding step the metal bases on the support are at least partially converted to the sulfide on treatment with $H_2S$ or elemental sulfur and hydrogen, if required, at elevated temperature. In the preferred sulfiding process, the dried catalyst-promoter-support system, prepared as described above, is charged to the process reactor to form a bed. Hydrogen sulfide gas is passed through the bed at about 350°–390° C. under atmopsheric or elevated pressure for several hours (e.g. 6–8 hours) until water of reaction is no longer present in the effluent gas stream. The sulfided catalyst system is then ready to use in the process.

The above described process provides enhanced conversions and yields of methyl mercaptan with lower reaction times at lower temperature and pressure conditions than heretofore experienced with similar processes, without the formation of substantial amounts of undesirable by-products.

I claim:

1. A continuous process for the manufacture of methyl mercaptan by contacting an intimate mixture of carbon oxide, sulfur or hydrogen sulfide, and hydrogen is elevated temperature and pressure at least sufficient to maintain sulfur in the molten state and at a carbon oxide space velocity of between about 5 and about 200 with a preformed single-phase, solid catalyst system comprising from about 10 to about 90%, based on the weight of said system, of a porous alumina-containing support and, upon which is deposited, from about 10 to 90%, based on the weight of said system, of a mixture of (a) from about 65 to about 95% based on the weight of said mixture, of at least one sulfide selected from the group consisting of sulfides of iron, nickel, zinc, chromium, cobalt and molybdenum, and (b) from about 5 to about 35%, based on the weight of said mixture, of an alkali metal sulfide.

2. The process of claim 1 wherein the temperature is at least about 250° C. and the pressure is at least about 150 psig.

3. The process of claims 1 or 2 wherein the support comprises activated alumina.

4. The process of claim 3 wherein (a) is nickel sulfide and (b) is cesium sulfide or potassium sulfide.

5. The process of claim 3 wherein (a) is a mixture of zinc sulfide and chromium sulfide and (b) is cesium sulfide.

6. The process of claim 3 wherein the reactants carbon oxide, hydrogen sulfide and hydrogen are fed to the reactor in a molar ratio, respectively, within the range of about 1/3/2 to about 1/8/8.

7. The process of claim 5 wherein (a) is a mixture of from about 50 to about 65% zinc sulfide and from about 35 to about 50% chromium sulfide, based on the weight of (a), mixture (a) is present in the catalyst system in an amount ranging from about 80 up to 95% and (b) is present in an amount ranging from about 5 to about 20% based on the combined weight of (a) and (b).

8. The process of claim 7 wherein (i) the temperature in the reactor is within the range of about 250° and about 400° C., (ii) the pressure in the reactor is within the range of about 400 and about 1000 psig, (iii) the reactants, carbon monoxide, hydrogen sulfide and hydrogen are reacted at a molar ratio respectively ranging from 1/3/2 to 1/8/8, and (iv) the reactants are at a temperature of at least 180° C. when fed to the reactor.

* * * * *